United States Patent [19]

Tanabe et al.

[11] Patent Number: 4,948,892
[45] Date of Patent: Aug. 14, 1990

[54] SULFONAMID COMPOUND USEFUL FOR TREATING CARDIOVASCULAR DISORDERS

[75] Inventors: Sohei Tanabe, Higashimurayama; Seiichi Sato, Tokyo; Yoshinori Kyotani, Higashiyamato; Tomio Ohta, Sayama; Yasumi Uchida, Ichikawa, all of Japan

[73] Assignee: Kowa Comp., Ltd., Nagoya, Japan

[21] Appl. No.: 310,684

[22] Filed: Feb. 15, 1989

[30] Foreign Application Priority Data

Feb. 18, 1988 [JP] Japan .................................. 63-33949

[51] Int. Cl.$^5$ .................. C07D 295/08; C07D 295/10; C07D 295/12
[52] U.S. Cl. .................................... 544/396; 544/360; 544/384; 544/385; 544/392; 544/394; 544/398
[58] Field of Search ............... 544/360, 384, 385, 392, 544/394, 396, 398

[56] References Cited

U.S. PATENT DOCUMENTS 3,880,644  4/1975  Beck ........................................ 71/88
4,132,786  1/1979  Moreau et al. ........................ 564/87
4,714,700  12/1987 Fournier et al. ..................... 544/398

FOREIGN PATENT DOCUMENTS 9495  3/1985  Japan .

OTHER PUBLICATIONS

Beck, Chem. Abst. 83-193109n (1975).
Lilly, Eli, & Co., Chem. Abst. 84-4812y (1976).
Lilly, Eli, and Co., Chem. Abst. 85-105409y (1976).
Descamps et al., Chem. Abst. 88-6709b (1978).
Bilfing, Chem. Abst. 95-61994k (1981).
Hidaka et al., Chem. Abst. 105-78925m (1986).
Sandoz, S. A., Chem. Abst. 107-39820v (1987).
March, Advanced Org. Chem., 3rd Edition, p. 445.

Primary Examiner—Cecilia Shen
Attorney, Agent, or Firm—Wenderoth, Lind & Ponack

[57] ABSTRACT

A sulfonamide compound represented by the following formula

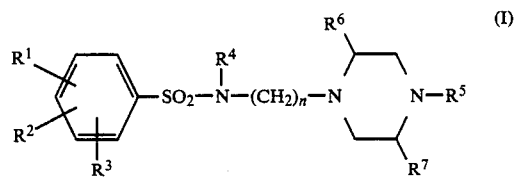

wherein $R^1$, $R^2$ and $R^3$ are identical or different, and each represents a hydrogen atom, a halogen atom, a lower alkyl group or a lower alkoxy group; $R^4$ represents a hydrogen atom, a lower alkyl group, or a substituted or unsubstituted aralykyl group; $R^5$ represents a substituted or unsubstituted aryl group or a substituted or unsubstituted aralkyl group; $R^6$ and $R^7$ are identical or different and each represents a hydrogen atom, a lower alkyl group or a lower alkoxy group; and n is an integer of 1 to 8, and an acid addition salt thereof. The compounds of formula (I) provided by this invention have some useful biological activities such as the spasmolytic activity on the vascular smooth muscles and anti-platelet aggregatory activity and are useful as drugs for treating cardiovascular disorders such as angina pectoris, cerebral circulation disorder and thrombosis.

8 Claims, No Drawings

SULFONAMID COMPOUND USEFUL FOR TREATING CARDIOVASCULAR DISORDERS

This invention relates to novel sulfonamide compounds, and more specifically, to a sulfonamide compound represented by the following formula

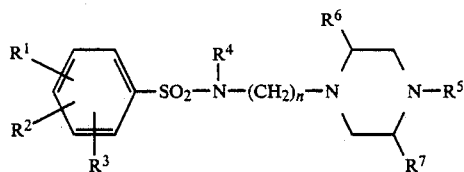

wherein $R^1$, $R^2$ and $R^3$ are identical or different, and each represents a hydrogen atom, a halogen atom, a lower alkyl group or a lower alkoxy group; $R^4$ represents a hydrogen atom, a lower alkyl group, or a substituted or unsubstituted aralkyl group; $R^5$ represents a substituted or unsubstituted aryl group or a substituted or unsubstituted aralkyl group; $R^6$ and $R^7$ are identical or different and each represents a hydrogen atom, a lower alkyl group or a lower alkoxy group; and n is an integer of 1 to 8, or an acid addition salt thereof, and to a process for production thereof.

omega-(Arylsulfonamide)alkylamines of the following formula

$$R'—SO_2NH(CH_2)_mR \quad (A)$$

wherein R represents an amino group or an acetylamino group, R' represents a phenyl or naphthyl group which may be substituted by a halogen atom or a lower alkyl group, and m is an integer of 6 to 8, have platelet aggregation inhibiting activity and are known to be useful for the prevention and treatment of thrombosis in a cerebrocardiovascular system (Japanese Patent Publication No. 9495/1985).

The compounds of formula (I) provided by this invention have some useful biological activities such as the spasmolytic activity on the vascular smooth muscles and anti-platelet aggregatory activity and are useful as drugs for treating cardiovascular disorders such as angina pectoris, cerebral circulation disorder and thrombosis.

In the present specification, the term "lower" used to qualify a group or compound, means that the group or compound so qualified has not more than 6, preferably not more than 4, carbon atoms.

The "lower alkyl group" in the present specification may be linear or branched, and includes, for example, methyl, ethyl, propyl, isopropyl, butyl, isobutyl, sec-butyl, tert-butyl, pentyl, isoamyl and hexyl groups. The "lower alkoxy group" is a lower alkyl-oxy group in which the lower alkyl moiety has the above meaning, and includes, for example, methoxy, ethoxy, propoxy, isopropoxy, butoxy, sec-butoxy, tert-butoxy and hexyloxy groups. The "halogen atom" includes fluorine, chlorine, bromine and iodine atoms.

The "aryl group" is an aromatic group which contains 5 to 20 carbon atoms and may be monocyclic or polycyclic and contain a heteroatom such as a nitrogen atom in the ring. Examples include phenyl, alpha-naphthyl, beta-naphthyl and pyridyl groups. The "aralkyl group" is an aryl-lower alkyl group in which the lower alkyl and aryl have the above meanings. Examples are benzyl, phenethyl, diphenylmethyl, triphenylmethyl, alpha-naphthylmethyl, beta-naphthylmethyl, alpha-naphthylethyl, beta-naphthylethyl groups.

The aryl and aralkyl groups may be substituted, and Examples of substituents include lower alkyl groups, lower alkoxy groups and halogen atoms. The aryl group or aralkyl group may be substituted by 1 to 3 such substituents.

In a preferred group of compounds of formula (I),
$R^1$, $R^2$ and $R^3$ are identical or different and each may represent a hydrogen atom, a fluorine atom, a chlorine atom or a $C_1$-$C_4$ alkyl group (preferably, a methyl group), $R^4$ may represent a hydrogen atom, a $C_1$-$C_4$ alkyl group (preferably a methyl group) or a benzyl group, $R^5$ may represent a benzyl, diphenylmethyl, triphenylmethyl or pyridyl group which may be substituted by 1 to 3 $C_1$-$C_4$ alkoxy (preferably methoxy) groups, $R^6$ and $R^7$ are identical or different and each may represent a hydrogen atom or a $C_1$-$C_4$ alkyl group (preferably methyl group), and n may be an integer of 2 to 6.

In a more preferred group of compounds of formula (I), $R^1$, $R^2$ and $R^3$ may simultaneously represent a hydrogen atom, or one of these groups may be a fluorine or chlorine atom and the remainder, hydrogen atoms, $R^4$ may represent a hydrogen atom or a benzyl group, $R^5$ may represent a benzyl or diphenylmethyl group, $R^6$ and $R^7$ may simultaneously be hydrogen atoms, and n may be an integer of 2 to 6.

Specific examples of the compounds of formula (I) are given below in addition to those given in the working examples hereinafter.

1-α-Naphthyl-2,6-diethyl-4-[N-ethyl-N-(3,5-dibromobenzenesulfonyl)aminomethyl]piperazine, 1-(3,4,5-trimethoxyphenyl)-4-8-N-(n-propyl)-N-(2,4,6-triethylbenzenesulfonyl)aminooctyl]piperazine, 1-p-chlorophenethyl-3,6-dimethoxy-4-2-N-(β-naphthylmethyl)-N-(3,5-diisopropylbenzenesulfonyl)-aminoethyl)piperazine, 1-(4-pyridylmethyl)-4-[7-N-isobutyl-N-(4-isobutylbenzenesulfonyl)amino-n-pentyl]piperazine, 1-(α-naphthyl)-4-[2-N-(p-chlorophenethyl)-N-(3,5-dimethoxybenzenesulfonyl)aminoethyl]piperazine, 1-diphenylethyl-4-3-N-(3,4,5-trimethoxybenzyl)-N-(2,6-dichloro-4-n-propylbenzenesulfonyl)amino-n-propyl)piperazine, 1-dibromobenzyl-3,6-di-n-propyl-4-5-N-(2-pyridylmethyl)-N-benzenesulfonylamino-n-pentyl]piperazine, and 1-(4-chloro-2,6-dimethoxyphenyl)-2-ethoxy-4-[4-N-(p-methylbenzyl)-N-benzenesulfonylamino-n-butyl)-6-ethylpiperazine.

The compounds of formula (I) may exist as acid addition salts. Examples of the acid addition salts are salts with inorganic acids such as sulfuric acid, hydrochloric acid, nitric acid, phosphoric acid and hydrobromic acid and salts with organic acids such as acetic acid, lactic acid, succinic acid, tartaric acid, malic acid, citric acid, methanesulfonic acid, benzenesulfonic acid and toluenesulfonic acid. Pharmaceutically acceptable acid addition salts are particularly preferred.

The compounds of formula (I) can be produced, for example, by the method shown in the reaction scheme A below.

Reaction Scheme A

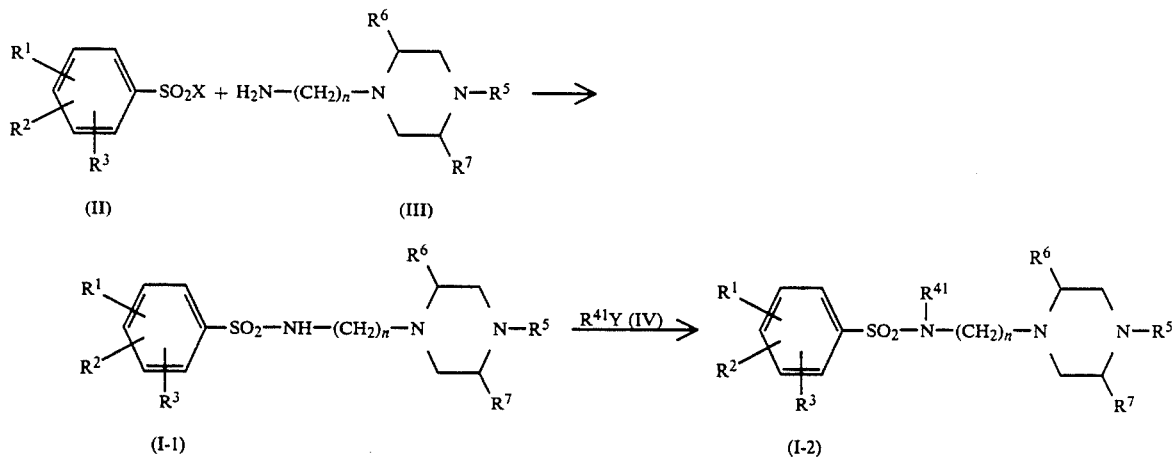

In the above formulae, $R^{41}$ represents the groups defined for $R^4$ excepting a hydrogen atom;

X represents a halogen atom;

Y represents a halogen atom, a lower alkylsulfonyloxy group, a substituted or unsubstituted arylsulfonyloxy group, or a nitroxy group; and $R^1$, $R^2$, $R^3$, $R^5$, $R^6$ and $R^7$ are as defined above.

In the method shown in the reaction scheme A, a compound of formula (I) in which $R^4$ is a hydrogen atom, i.e. a compound of formula (I-1), can be obtained by reacting an arylsulfonyl halide of formula (II) with a piperazine compound of formula (III). This reaction can be carried out usually in a suitable solvent, preferably in the presence of a base, at a temperature of about $-10°$ C. to the refluxing temperature of the reaction mixture, preferably about 0° to about 30° C. Examples of the solvent that can be used in this reaction include halogenated hydrocarbons such as methylene chloride, chloroform and carbon tetrachloride, hydrocarbon such as benzene, toluene and cyclohexane, ketones such as acetone and methyl ethyl ketone, ethers such as methyl ethyl ether, diethyl ether, dioxane and tetrahydrofuran, acetonitrile, dimethylformamide and dimethyl sulfoxide. Examples of the base that may be used as required include inorganic bases such as sodium hydride, potassium hydride, sodium hydroxide, potassium hydroxide, sodium carbonate, and potassium carbonate, and organic bases such as triethylamine, dimethylaminopyridine and pyrrolidinopyridine.

The proportion of the compound of formula (III) used relative to the compound of formula (II) is not critical and may be varied over a wide range depending upon the reaction conditions, for example. Generally, the compound of formula (III) may be conveniently used in a proportion of 1 to 10 moles, preferably 1 to 2 moles, per mole of the compound of formula (II).

As a result, the compound of formula (I-1) is obtained. By reacting this compound with an alkylating agent of formula (IV), a compound of formula (I) in which $R^4$ represents the groups defined above excepting hydrogen, i.e. a compound of formula (I-2), can be obtained.

Usually, the reaction of the compound of formula (I-1) with the compound of formula (IV) may be carried out in the solvent exemplified above, preferably in the presence of the base exemplified above, at a temperature of about $-10°$ to about 150° C., preferably about 0° to about 100° C. The amount of the compound of formula (V) relative to the compound of formula (I-1) is not critical. Generally, the compound of formula (IV) is suitably used in an amount of 1 to 10 moles, preferably 1 to 2 moles, per mole of the compound of formula (I-1).

The compounds of formula (I-1) and formula (I-2) can be isolated from the reaction mixture and/or purified by conventional methods such as recrystallization, extraction and chromatography.

As required, the compounds of formula (I) may be converted into acid addition salts by treating them with the aforesaid inorganic acids or organic acids.

As stated above, the compounds of formula (I) provided by this invention have excellent biological activities on a cardiovascular system, such as the spasmolytic activity on the vascular smooth muscles and anti-platelet aggregatory activity, and are expected to be useful drugs for preventing and treating diseases such as angina pectoris and cerebral circulation disorder. There is now a tendency that laser angioplasty will be put into practice in the near future for the treatment of arterial thrombosis. The most significant problem is the spasmodic contraction which occurs during the laser angioplasty. Therefore, the compounds (I) of this invention which have spasmolytic activity on blood vessels will effectively support the operation of thrombosis.

The spasmolytic activity on the vascular smooth muscles and anti-platelet aggregatory activity of the compounds of this invention can be demonstrated by the following in vitro and in vivo tests.

(A) Inhibitory activity on spasmodic contraction

Ring segments 2 mm wide, were prepared from the coronary artery (left circumflex coronary artery or anterior descending artery having a diameter of about 2 to 3 mm isolated from male dogs). The ring segments were each suspended in a Magnus tube filled with 20 ml of the Krebs-Henseleit solution (37° C., 95% $O_2$—5% $CO_2$ were passed) at an initial, tension of 2 g. The tension was measured by a U gauge. After standing for more than 30 minutes to stabilize the segments 25 or 50 mM KCl was added 2 to 3 times at intervals of 15 minutes to test the reactivity of the sample segments. 10 mM 3,4-diaminopyridine (a product of Nakarai Chemical Co. Ltd.) was added to those samples which showed a good contracting reaction to induce periodic contraction. When the periodic contraction became nearly constant, test compounds were added cumulatively, and their activity was examined.

(B) Inhibitory effect on ADP-induced platelet aggregation

Rabbit PRP (250 μl) was preincubated with drug samples (10 μl of aqueous solution or 1 μl of DMSO solution) at 37° C. for 1 minute, and ADP (2 μM)-induced platelet aggregation was measured by aggregometer (NKK HEMA TRACER1 Model PAT-4M). Inhibitory effects of the drugs were estimated from the standard curve of maximal aggregation.

The results are summarized in the following table.

| Compound No. (Example No.) | Spasmodic contraction inhibitory concentration (mole/liter) | Platelet aggregation inhibitory concentration (mole/liter) Inhibition rate (%) in the parentheses |
|---|---|---|
| 1 | $10^{-6}$ | |
| 4 | $10^{-6}$ | $10^{31\ 4}$ (40) |
| 8 | $10^{-6}$ | |
| 9 | $10^{-6}$ | $10^{-4}$ (3) |
| 12 | $10^{-6}$ | |
| 13 | $10^{-6}$ | |

The following examples illustrate the present invention more specifically.

EXAMPLE 1

Production of 1-diphenylmethyl-4-(3-benzenesulfonylaminopropyl)-piperazine 85 mg of 1-diphenylmethyl-4-(3-aminopropyl)-piperazine and 102.5 mg of triethylamine were added to ml of methylene chloride, and under ice cooling and stirring, 39.4 mg of benzenesulfonyl chloride was added. The mixture was further stirred at this temperature for 1 hour. Chloroform was added to the reaction mixture, and the mixture was then washed with water and dried. The solvent was then evaporated to give 115 mg of the captioned compound as a crude product. It was converted to a dihydrochloride in a customary manner, and recrystallization from ethanol/ether gave 92.7 mg of the captioned compound as a colorless powdery crystal having a melting point of 160° to 165° C. (decomp.).

IR: $\nu_{max}^{KBr}$, cm$^{-1}$
3408, 1444, 1329, 1158, 1091
$^1$H-NMR: δ CDCl$_3$
7.90–7.38 (15H, m, aromatic H)

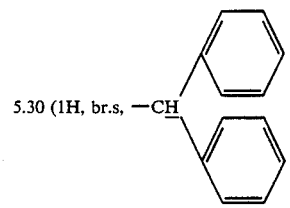

5.30 (1H, br.s, —CH

EXAMPLE 2

Production of 1-diphenylmethyl-4-3-(N-benzyl-benzenesulfonylamino)propyl)piperazine The compound obtained in Example 1 (140 mg) was dissolved in 3 ml of dimethylformamide, and with ice cooling and stirring, 30 mg of 40% sodium hydride was added. Then, 90.9 mg of benzyl bromide was added, and the mixture was stirred at this temperature for 1 hour. An aqueous solution of ammonium chloride was added to the reaction mixture, and the mixture was extracted with ethyl acetate. The extract was washed with water, and the solvent was evaporated to give 237 mg of a crude product. When the crude product was purified by preparative thin-layer chromatography [carrier:silica gel; solvent:chloroform/methanol (20:1)] 156 mg of the desired free base was obtained. This compound was converted into a dihydrochloride in a customary manner. Recrystallization from ethanol/ether gave 123.7 mg of a pale yellow powdery crystal having a melting point of 120° to 125° C. (decomp.)

IR: $\nu_{max}^{KBr}$, cm$^{-1}$
3414, 1454, 1331, 1155, 706
$^1$H-NMR: δ CDCl$_3$
8.00–7.30 (20H, m, aromatic H)

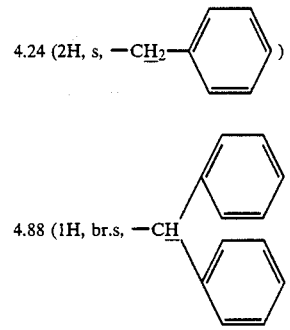

4.24 (2H, s, —CH$_2$— )

4.88 (1H, br.s, —CH

EXAMPLES 3–19

The compounds of formula (I) tabulated below were produced in the same way as in Examples 1 and 2.

| Example | R$^1$, R$^2$, R$^3$ | R$^4$ | R$^5$ | R$^6$ | R$^7$ | n | Melting point (°C.) |
|---|---|---|---|---|---|---|---|
| 3 | H | H | —CH$_2$—⌬ | H | H | 3 | 206–211 (decomp.) (dihydrochloride) |
| 4 | H | —CH$_2$—⌬ | " | H | H | 3 | 197–200 (decomp.) (dihydrochloride) |

-continued

| Example | R¹, R², R³ | R⁴ | R⁵ | R⁶ | R⁷ | n | Melting point (°C.) |
|---|---|---|---|---|---|---|---|
| 5 | H | H | 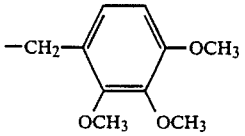 | H | H | 3 | 230–232 (decomp.) (dihydrochloride) |
| 6 | 4-Cl | H | " | H | H | 3 | 223–224 (decomp.) (dihydrochloride) |
| 7 | H | H | 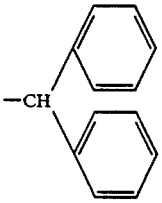 | H | H | 2 | 196–198 (decomp.) (dihydrochloride) |
| 8 | 4-F | H | " | H | H | 3 | 150–154 (decomp.) (dihydrochloride) |
| 9 | 4-Cl | H | " | H | H | 3 | 150–154 (decomp.) (dihydrochloride) |
| 10 | H | —CH₃ | " | H | H | 3 | 195–198 (decomp.) (dihydrochloride) |
| 11 | H | H | " | H | H | 4 | 126–132 (decomp.) (dihydrochloride) |
| 12 | H | H | 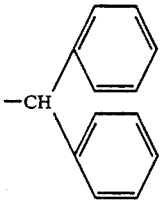 | H | H | 5 | 195–198 (decomp.) (dihydrochloride) |
| 13 | H | H | " | H | H | 6 | 190–193 (decomp.) (dihydrochloride) |
| 14 | H | H | 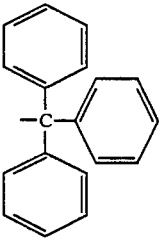 | H | H | 6 | 165–166 (decomp.) (maleate) |
| 15 | H | H | " | H | H | 3 | 126–131 (decomp.) (maleate) |
| 16 | H | H | 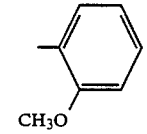 | H | H | 6 | 145–148 (decomp.) (dihydrochloride) |
| 17 | H | H | 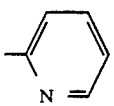 | H | H | 3 | 120–129.5 (free base) |

-continued

| Example | R¹, R², R³ | R⁴ | R⁵ | R⁶ | R⁷ | n | Melting point (°C.) |
|---|---|---|---|---|---|---|---|
| 18 | H | H | 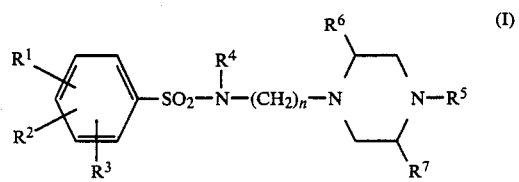 | CH₃ | CH₃ | 3 | 169–171 (decomp.) (dihydrochloride) |
| 19 | 2,4,6-tri-CH₃ | H | " | " | " | 3 | 186–188.5 (decomp.) (dihydrochloride) |

We claim:

1. A sulfonamide compound represented by the following formula $$\begin{array}{c}R^1\\R^2\end{array}\!\!\!\!\bigcirc\!\!-SO_2-\underset{R^4}{N}-(CH_2)_n-N\underset{R^7}{\overset{R^6}{\bigcirc}}N-R^5 \quad (I)$$

wherein $R^1$, $R^2$ and $R^3$ are identical or different, and each represents a hydrogen atom, a halogen atom, a lower alkyl group or a lower alkoxy group; $R^4$ represents a hydrogen atom, a lower alkyl group or a lower alkyl group substituted by 1 to 3 phenyl or naphthyl groups the ring of which may be substituted by 1 to 3 substituents selected from the group consisting of lower alkyl groups, lower alkoxy groups and halogen atoms; $R^5$ represents a phenyl, naphthyl or pyridyl group the ring of which may be substituted by 1 to 3 substituents selected from the group consisting of a lower alkyl group, a lower alkoxy group and a halogen atom or a lower alkyl group substituted by 1 to 3 phenyl or naphthyl groups the ring of which may be substituted by 1 to 3 substituents selected from the group consisting of a lower alkyl group, a lower alkoxy group and a halogen atom; $R^6$ and $R^7$ are identical or different and each represents a hydrogen atom, a lower alkyl group or a lower alkoxy group; and n is an integer of 1 to 8, and an acid addition salt thereof.

2. The compounds of claim 1 in which $R^1$, $R^2$ and $R^3$ are identical or different and each represents a hydrogen atom, a fluorine atom, a chlorine atom or an alkyl group having 1 to 4 carbon atoms.

3. The compounds of claim 1 in which $R^4$ represents a hydrogen atom, an alkyl group having 1 to 4 carbon atoms, or a benzyl group.

4. The compounds of claim 1 in which $R^5$ represents a phenyl benzyl, diphenylmethyl, triphenylmethyl or pyridyl group which may be substituted by 1 to 3 alkoxy groups having 1 to 4 carbon atoms.

5. The compounds of claim 1 in which $R^6$ and $R^7$ are identical or different and each represents a hydrogen atom or an alkyl group having 1 to 4 carbon atoms.

6. The compounds of claim 1 in which n is an integer of 2 to 6.

7. The compounds of claim 1 in which $R^1$, $R^2$ and $R^3$ are simultaneously hydrogen atoms, or one of them is a fluorine or chlorine atom, and the remainder are hydrogen atoms; $R^4$ represents a hydrogen atom or a benzyl group; $R^5$ represents a benzyl or diphenyl methyl group; $R^6$ and $R^7$ are both hydrogen atoms; and n is an integer of 2 to 6.

8. The compound of claim 1 which is:
1-diphenylmethyl-4-(3-benzenesulfonylaminopropyl)-piperazine, 1-benzyl-4-(3-N-benzylbenzenesulfonylaminopropyl)-piperazine, 1-diphenylmethyl-4-[3-(4-fluorobenzend)sulfonylaminopropyl]piperazine, 1-diphenylmethyl-4-[3-(4-chlorobenzene)sulfonylaminopropyl]piperazine, 1-diphenylmethyl-4-(5-benzenesulfonylamino-n-pentyl)piperazine or 1-diphenylmethyl-4-(6-benzenesulfonylamino-n-hexyl)piperazine.

* * * * *